US012100516B2

(12) United States Patent
Bernard et al.

(10) Patent No.: US 12,100,516 B2
(45) Date of Patent: Sep. 24, 2024

(54) MICROFLUIDIC CORONARY CIRCULATORY MODEL

(71) Applicants: Andre Bernard, St. Gallen (CH); Peter Heeb, Balgach (CH); Cornelia Nef, Gams (CH); Dominik Obrist, Suhr (CH); Francesco Clavica, Derendingen (CH); Sabrina Frey, Bern (CH); Robert S. Schwartz, Inver Grover Heights, MN (US); Jon Helge Hoem, Baar (CH); Oliver Bludau, Baar (CH)

(72) Inventors: Andre Bernard, St. Gallen (CH); Peter Heeb, Balgach (CH); Cornelia Nef, Gams (CH); Dominik Obrist, Suhr (CH); Francesco Clavica, Derendingen (CH); Sabrina Frey, Bern (CH); Robert S. Schwartz, Inver Grover Heights, MN (US); Jon Helge Hoem, Baar (CH); Oliver Bludau, Baar (CH)

(73) Assignee: CorFlow Therapeutics AG, Baar (CH)

( * ) Notice: Subject to any disclaimer, the term of this patent is extended or adjusted under 35 U.S.C. 154(b) by 969 days.

(21) Appl. No.: 17/059,190

(22) PCT Filed: May 31, 2019

(86) PCT No.: PCT/US2019/035020
§ 371 (c)(1),
(2) Date: Nov. 25, 2020

(87) PCT Pub. No.: WO2019/232452
PCT Pub. Date: Dec. 5, 2019

(65) Prior Publication Data
US 2021/0366620 A1 Nov. 25, 2021

Related U.S. Application Data

(60) Provisional application No. 62/678,546, filed on May 31, 2018.

(51) Int. Cl.
*G16H 50/50* (2018.01)
*G06F 30/20* (2020.01)

(52) U.S. Cl.
CPC ............. *G16H 50/50* (2018.01); *G06F 30/20* (2020.01)

(58) Field of Classification Search
CPC ................................ G16H 50/50; G06F 30/20
See application file for complete search history.

(56) References Cited

U.S. PATENT DOCUMENTS

| 4,689,041 A | 8/1987 | Corday et al. |
| 6,156,005 A | 12/2000 | Theron |

(Continued)

FOREIGN PATENT DOCUMENTS

| AU | 2017205404 A1 | 7/2018 |
| CA | 3010447 A1 | 7/2017 |

(Continued)

OTHER PUBLICATIONS

Costa et al. Mimicking Arterial Thrombosis in A 3D-Printed Microfluidic In Vitro Vascular Model Based on Computed Tomography Angiography Data Lab Chip, 2017.17 pp. 2785-2792 (Year: 2017).*

(Continued)

*Primary Examiner* — Rehana Perveen
*Assistant Examiner* — Cuong V Luu
(74) *Attorney, Agent, or Firm* — Eversheds Sutherland (US) LLP; Regis C. Worley, Jr.; Nicola A. Pisano

(57) ABSTRACT

Systems, methods and apparatus are included that are configured to model microvascular obstruction (MVO) in patients. According to one aspect of the present disclosure, a multi-scale model is configured to mimic myocardial microcirculation of coronary vessels. The model includes collaterals configured to provide alternative pathways possibly bypassing the MVO, and configured to model coronary (Continued)

artery compliance for spatially resolved fluid transport through the coronary vessels. The model is configured to simulate the MVO by increasing flow resistance in at least one of the modelled coronary vessels, or by blocking the at least one of the modelled coronary vessels completely. The model is also configured to mimic behavior of fluid transport in the coronary vessels during diagnostics or treatment, to design and optimize therapy protocols for the MVO.

21 Claims, 14 Drawing Sheets

(56) References Cited

U.S. PATENT DOCUMENTS

| | | |
|---|---|---|
| 6,295,990 B1 | 10/2001 | Lewis et al. |
| 6,423,032 B2 | 7/2002 | Parodi |
| 6,485,500 B1 | 11/2002 | Kokish et al. |
| 6,488,671 B1 | 12/2002 | Constantz et al. |
| 7,722,596 B2 | 5/2010 | Shapland et al. |
| 7,837,650 B1 | 11/2010 | Cox et al. |
| 8,177,704 B1 | 5/2012 | Mohl et al. |
| 8,366,659 B2 | 2/2013 | Ehrenreich et al. |
| 8,430,861 B2 | 4/2013 | Schwartz et al. |
| 8,540,669 B2 | 9/2013 | Ehrenreich et al. |
| 8,708,996 B2 | 4/2014 | Consigny et al. |
| 8,876,850 B1 | 11/2014 | Vollmers et al. |
| 9,174,020 B2 | 11/2015 | Allen et al. |
| 9,205,226 B2 | 12/2015 | Allen |
| 9,320,846 B2 | 4/2016 | Burns et al. |
| 9,433,381 B2 | 9/2016 | Mohl et al. |
| 9,433,761 B2 | 9/2016 | Schwartz et al. |
| 9,550,046 B1 | 1/2017 | Allen et al. |
| 9,844,383 B2 | 12/2017 | Allen |
| 9,855,049 B2 | 1/2018 | Schiemanck et al. |
| 9,999,718 B2 | 6/2018 | Brady et al. |
| 10,118,016 B2 | 11/2018 | Schwartz et al. |
| 10,315,016 B2 | 6/2019 | Schwartz et al. |
| 10,952,883 B2 | 3/2021 | Hoem et al. |
| 11,135,408 B2 | 10/2021 | Schwartz et al. |
| 2001/0041862 A1 | 11/2001 | Glickman |
| 2002/0115982 A1 | 8/2002 | Barbut et al. |
| 2004/0260333 A1 | 12/2004 | Dubrul et al. |
| 2005/0049451 A1 | 3/2005 | Schock et al. |
| 2005/0245894 A1 | 11/2005 | Zadno-Azizi |
| 2005/0245897 A1 | 11/2005 | Bolduc et al. |
| 2005/0267561 A1 | 12/2005 | Jones et al. |
| 2008/0300573 A1 | 12/2008 | Consigny et al. |
| 2009/0177183 A1 | 7/2009 | Pinkernell et al. |
| 2010/0168649 A1 | 7/2010 | Schwartz et al. |
| 2010/0249704 A1 | 9/2010 | Wagner |
| 2010/0280451 A1 | 11/2010 | Teeslink et al. |
| 2011/0196255 A1 | 8/2011 | Kassab |
| 2012/0072190 A1* | 3/2012 | Sharma .......... A61B 5/026 703/2 |
| 2012/0157913 A1 | 6/2012 | Aziz et al. |
| 2012/0265079 A1 | 10/2012 | Hilmersson |
| 2012/0265283 A1 | 10/2012 | Mack et al. |
| 2013/0035560 A1 | 2/2013 | Anand et al. |
| 2013/0132054 A1* | 5/2013 | Sharma .......... G16H 30/40 703/9 |
| 2013/0165858 A1 | 6/2013 | Cox et al. |
| 2014/0323887 A1 | 10/2014 | Anderson et al. |
| 2015/0133799 A1 | 5/2015 | O'Connell et al. |
| 2015/0141853 A1 | 5/2015 | Miller, III et al. |
| 2016/0082178 A1 | 3/2016 | Agah et al. |
| 2016/0199003 A1 | 7/2016 | McCaffrey et al. |
| 2016/0213834 A1 | 7/2016 | Brady et al. |
| 2016/0270731 A1 | 9/2016 | Burkett |
| 2016/0361068 A1 | 12/2016 | Mohl et al. |
| 2017/0189654 A1 | 7/2017 | Schwartz et al. |
| 2017/0290598 A1 | 10/2017 | Culbert et al. |
| 2018/0146864 A1 | 5/2018 | Jansen et al. |
| 2018/0185576 A1 | 7/2018 | Burns et al. |
| 2018/0280172 A1 | 10/2018 | Hoem et al. |
| 2018/0353681 A1 | 12/2018 | Burmaster et al. |
| 2019/0046760 A1 | 2/2019 | Schwartz et al. |
| 2019/0082976 A1 | 3/2019 | Hoem et al. |
| 2019/0275248 A1 | 9/2019 | Schwartz et al. |
| 2019/0290889 A1 | 9/2019 | De Bruyne et al. |
| 2019/0358437 A1 | 11/2019 | Schwartz et al. |
| 2020/0093991 A1 | 3/2020 | Schwartz et al. |
| 2020/0282189 A1 | 9/2020 | Gaynor |
| 2020/0316348 A1 | 10/2020 | Ascher et al. |
| 2020/0383688 A1 | 12/2020 | Olson et al. |
| 2021/0228387 A1 | 7/2021 | Hoem et al. |
| 2021/0361170 A1 | 11/2021 | Schwartz et al. |
| 2021/0366620 A1 | 11/2021 | Bernard et al. |

FOREIGN PATENT DOCUMENTS

| | | |
|---|---|---|
| CN | 201058169 Y | 5/2008 |
| CN | 103826690 A | 5/2014 |
| CN | 108778149 A | 11/2018 |
| EP | 3399923 A1 | 11/2018 |
| EP | 3399923 A4 | 8/2019 |
| GB | 2541368 A | 2/2017 |
| JP | 2006187620 A | 7/2006 |
| JP | 2009233175 A | 10/2009 |
| JP | 2013146505 A | 8/2013 |
| JP | 2014529417 A | 11/2014 |
| JP | 2015502237 A | 1/2015 |
| JP | 2015522347 A | 8/2015 |
| JP | 2016168151 A | 9/2016 |
| JP | 2016215836 A | 12/2016 |
| JP | 2017510412 A | 4/2017 |
| JP | 2018523506 A | 8/2018 |
| JP | 2019502522 A | 1/2019 |
| WO | WO-9600596 A1 | 1/1996 |
| WO | WO-0128419 A2 | 4/2001 |
| WO | WO-0170325 A2 | 9/2001 |
| WO | WO-02085443 A1 | 10/2002 |
| WO | WO-2004062526 A2 | 7/2004 |
| WO | WO-2006059317 A1 | 6/2006 |
| WO | WO-2008088579 A2 | 7/2008 |
| WO | WO-2014106158 A1 | 7/2014 |
| WO | WO-2015108928 A1 | 7/2015 |
| WO | WO-2015150913 A2 | 10/2015 |
| WO | WO-2017004432 A1 | 1/2017 |
| WO | WO-2017078693 A1 | 5/2017 |
| WO | WO-2017120229 A1 | 7/2017 |
| WO | WO-2017160270 A1 | 9/2017 |
| WO | WO-2017210584 A1 | 12/2017 |
| WO | WO-2018175485 A1 | 9/2018 |
| WO | WO-2019060421 A1 | 3/2019 |
| WO | WO-2019173758 A1 | 9/2019 |
| WO | WO-2019232452 A1 | 12/2019 |

OTHER PUBLICATIONS

Tsai et al. In vitro modeling of the microvascular occlusion and thrombosis that occur in hematologic diseases using microfluidic technology The journal of Clinical Investigation, vol. 122 No. Jan. 1, 2012 (Year: 2012).*
Kim et al. Vasculature-On-A-Chip for Invitro Disease Models Bioengineering, Jan. 24, 2017 (Year: 2017).*
Chung et al. Microfluidic Fabrication of Microengineered Hydrogels and Their Application In Tissue Engineering, Lab Chip, Nov. 12, 2012 (Year: 2012).*
Costa, et al., "Mimicking Arterial Thrombosis in a 3d-printed Microfluidic in Vitro Vascular Model Based on Computed Tomography Angiography Data," Lab on a Chip, Royal Society of Chemistry, 17(16):2785-2792 (2017).
Extended European Search Report dated Jul. 19, 2019 in EP Patent Appl. Serial No. 17736254.8.
International Preliminary Report on Patentability dated Apr. 2, 2020 in Int'l PCT Patent Application Serial No. PCT/US2018/051760.
International Preliminary Report on Patentability dated Sep. 15, 2020 in Int'l PCT Patent Application Serial No. PCT/US2019/021426.

(56) References Cited

OTHER PUBLICATIONS

International Search Report and Written Opinion dated Oct. 1, 2019 in Int'l PCT Patent Application Serial No. PCT/US2019/035020.
International Search Report and Written Opinion dated Jan. 3, 2019 in Int'l PCT Patent Application Serial No. PCT/US2018/051760.
International Search Report and Written Opinion dated Mar. 17, 2017 in Int'l PCT Patent Application Serial No. PCT/US2017/012181.
International Search Report and Written Opinion dated May 25, 2018 in Int'l PCT Patent Application Serial No. PCT/US2018/023422.
International Search Report and Written Opinion dated Jul. 3, 2019 in Int'l PCT Patent Application Serial No. PCT/US2019/021426.
International Search Report and Written Opinion dated Nov. 27, 2019 in Int'l PCT Patent Application Serial No. PCT/US2019/052245.
Lindsey, et al., "Guidelines for Experimental Models of Myocardial Ischemia and Infarction," American Journal of Physiology-Heart and Circulatory Physiology, 314(4):H812-H838 (2018).
Liu, JingHua, Coronary Heart Disease: Anatomy, Function and Imaging, Peking Union Medical College Press, Apr. 30, 2013, p. 56.
Qiu, et al., "Microvasculature-on-a-Chip for the Long-term Study of Endothelial Barrier Dysfunction and Microvascular Obstruction in Disease," Nature Biomedical Engineering, 2(6):453-463 (2018).
Supplementary European Search Report dated Apr. 24, 2020 in EP Patent Appl. Serial No. 18771178.3.
Tsai, et al., "In Vitro modeling of the microvascular occlusion and thrombosis that occur in hematologic diseases using microfluidic technology," Journal of Clinical Investigation, 122(1):408-418 (2012).
International Search Report & Written Opinion dated Apr. 7, 2022 in Int'l PCT Patent Appl. Serial No. PCT/IB2022/050152.
International Search Report & Written Opinion dated Aug. 9, 2021 in Int'l PCT Patent Appl. Serial No. PCT/IB2021/054453.
U.S. Appl. No. 15/398,470 / U.S. Pat. No. 10,315,016, filed Jan. 4, 2017 / Jun. 11, 2019.
U.S. Appl. No. 15/926,911, filed Mar. 20, 2018.
U.S. Appl. No. 16/135,987, filed Sep. 19, 2018.
U.S. Appl. No. 16/297,339, filed Mar. 8, 2019.
U.S. Appl. No. 16/413,436, filed May 15, 2019.
U.S. Appl. No. 16/577,962, filed Sep. 20, 2019.

\* cited by examiner

CHIP DESIGN AND FABRICATION
MORPHOMETRY OF (PIG) CORONARY ARTERIAL TREES

| ORDER | DIAMETER [μm] | LENGTH [μm] | NUMBER |
|---|---|---|---|
| 1 | 9.2 | 56 | 923'339 |
| 2 | 13.0 | 72 | 339'873 |
| 3 | 18.7 | 72 | 115'638 |
| 4 | 34.6 | 112 | 46'194 |
| 5 | 71.6 | 454 | 16'093 |
| 6 | 150 | 609 | 3'524 |
| 7 | 303 | 920 | 909 |
| 8 | 467 | 1090 | 283 |
| 9 | 715 | 1540 | 83 |
| 10 | 1'492 | 2'260 | 18 |
| 11 | 3'176 | 2'820 | 2 |

- Orders 1–4: NOT YET INCLUDED → LUMPED COMPLAINT AND VALVES
- Orders 5–9: MICROFLUIDIC CHIP
- Orders 10–11: FITTINGS, TUBINGS
- Orders 5–11: AIM INTEGRATED DEVICE

FIG. 3

CHIP DESIGN AND FABRICATION
FLUID CHIP LAYOUT
(SIZE 28X38MM)

CHANNEL HIERARCHY AND DIMENSIONS

| ORDER | 5 | 6 | 7 | 8 | 9 | 10 | BASSIN |
|---|---|---|---|---|---|---|---|
| WIDTH/µM | 300 | 300 | 300 | 600 | 600 | | |
| HEIGHT/µM | 41 | 100 | 306 | 382 | 885 | | 1500 |
| LENGTH/µM | 454 | 609 | 920 | 1'090 | 9'030 | 20'300 | |
| HYDR. DIAM./µM | 71.6 | 150 | 303 | 467 | 715 | 1492 | |

MICROFLUIDIC CORONARY CIRCULATORY MODEL

CLAIM OF PRIORITY AND INCORPORATION BY REFERENCE

This application is a national phase application under 35 U.S.C. § 371 of PCT/US2019/035020, filed May 31, 2019, which claims the benefit under 35 U.S.C. § 119(e) of U.S. Provisional Patent Application 62/678,546, filed May 31, 2018, the entire contents of each of which are hereby incorporated by reference herein in their entirety.

TECHNICAL FIELD

The present disclosure relates to circulatory models, and in particular to systems, apparatus and methods for a multi-scale microfluidic circulatory model for coronary circulation.

BACKGROUND

Heart attack or STEMI ('STEMI' defined as acute electrocardiogram (ECG) ST segment myocardial infarction) is caused by sudden occlusion of an epicardial coronary artery, typically by fibrin and platelet rich clot, with associated and embolic plaque and debris. Electrocardiographic signs of acute transmural myocardial infarction (heart attack) are ECG tracings with ST segment elevation (STEMI). ST segment elevation is a hallmark of severe coronary artery narrowing, often with occlusion causing ongoing ischemic myocardial injury with cell death. Large vessel occlusion is often associated with small vessel or stenosis occlusion (termed microvascular obstruction or MVO) by clot and embolic debris, also a serious problem since the heart muscle is deprived of blood, oxygen, and critical nutrients necessary to sustain cell life.

Ischemia occurs when part of the heart muscle, the myocardium, is deprived of oxygen and nutrients. Common causes of ischemia are narrowing or obstruction of a coronary artery, or a rapid arrhythmia, causing an imbalance in supply and demand for energy. A short period of ischemia causes reversible effects, and the heart cells are able to recover. When the episode of ischemia lasts for a longer period of time, heart muscle cells die. This is called a heart attack or myocardial infarction (MI). Hence, it is critical to recognize ischemia on the ECG in an early stage.

Interventional cardiology is very proficient at opening severely narrowed or occluded epicardial coronary arteries in the cardiac catheterization laboratory using catheters, guide wires, balloons, and stents. However, MVO cannot be diagnosed in the catheter laboratory, and more importantly MVO cannot be treated even if/when it could be accurately diagnosed.

STEMI therapy research has shown that, opening the epicardial/large coronary artery is insufficient to salvage heart muscle and optimize long term patient outcome. The most common reason for poor late results after heart attack is MVO. MVO is occlusion or severe flow limitation in the internal cardiac microvessels, typically by clot. These microvessels are impervious to stenting and conventional thrombolytic therapy. Thus, despite a widely patent epicardial coronary artery, residual MVO obstructs blood flow into the heart causing cell ischemia death from severe heart muscle damage.

MVO thus remains a critical frontier in cardiology. Cardiac microvessels comprise small arteries, arterioles, capillaries and venules which are frequently filled with clot and debris (platelets, fibrin, and embolic plaque material) during STEMI. Too often, obstructed microvessels not resolve even after stent placement, and have serious long-term negative prognostic implications.

There is a need in the art for apparatus and methods that can model MVO in heart attack patients.

SUMMARY

The present subject matter provides devices, systems and methods for diagnosing and treating MVO by modeling physiological and pathological conditions. Various examples are now described to introduce a selection of concepts in a simplified form that are further described below in the detailed description. The Summary is not intended to identify key or essential features of the claimed subject matter, nor is it intended to be used to limit the scope of the claimed subject matter.

According to one aspect of the present disclosure, a multi-scale model is configured to mimic myocardial microcirculation of coronary vessels. The model includes collaterals configured to provide alternative pathways bypassing a microvascular obstruction (MVO), and configured to model coronary artery compliance for spatially resolved fluid transport through the coronary vessels. The model is configured to simulate the MVO by increasing flow resistance in at least one of the modelled coronary vessels, or by blocking the at least one of the modelled coronary vessels completely. The model is also configured to mimic behavior of fluid transport in the coronary vessels during diagnostics or treatment, to design and optimize therapy protocols for the MVO.

According to another aspect of the present disclosure, method for modeling an MVO is provided. The method includes modeling myocardial microcirculation of coronary vessels using a multi-scale model, the multi-scale model including collaterals configured to model coronary arterial trees. The collaterals are configured to provide alternative pathways bypassing the MVO, and configured to model coronary artery compliance for spatially resolved fluid transport through the coronary vessels, in various embodiments. The MVO is simulated by increasing flow resistance in at least one of the modeled coronary vessels, in an embodiment.

According to another aspect of the present disclosure, an apparatus for modeling a microvascular obstruction (MVO) is provided. The apparatus includes a fluidic chip configured to mimic myocardial microcirculation of coronary vessels, and collaterals within the fluidic chip. The collaterals are configured to model coronary arterial trees, and configured to provide alternative pathways bypassing the MVO. The collaterals are configured to model coronary artery compliance for spatially resolved fluid transport through the coronary vessels, in various embodiments. The apparatus is configured to simulate the MVO by increasing flow resistance in at least one of the modeled coronary vessels, in an embodiment.

This Summary is an overview of some of the teachings of the present application and not intended to be an exclusive or exhaustive treatment of the present subject matter. Further details about the present subject matter are found in the detailed description and appended claims. The scope of the present inventive subject matter is defined by the appended claims and their legal equivalents.

BRIEF DESCRIPTION OF THE DRAWINGS

The present disclosure is illustrated by way of example and not limitation in the figures of the accompanying drawings, in which like references indicate similar elements and in which:

FIG. 3 illustrates morphometry of coronary arterial trees for use in device fabrication, according to various embodiments;

DETAILED DESCRIPTION

Figure 1:
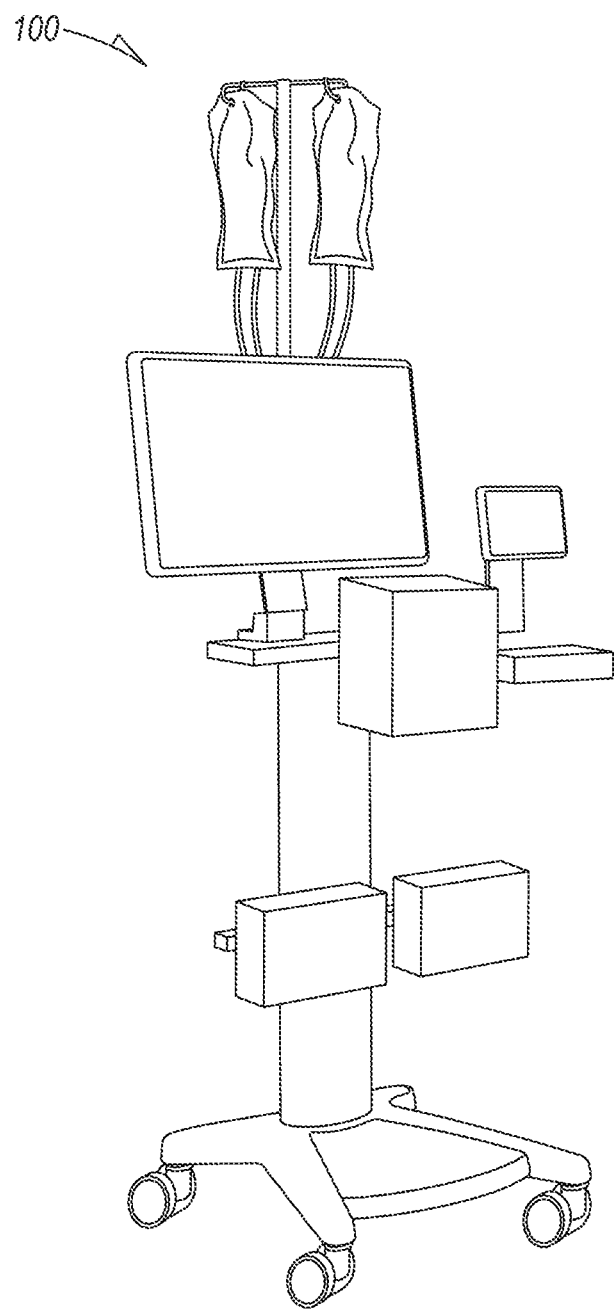
FIG. 1 illustrates an apparatus for MVO diagnosis and therapy, according to various embodiments.

The following detailed description of the present subject matter refers to subject matter in the accompanying drawings which show, by way of illustration, specific aspects and embodiments in which the present subject matter may be practiced. These embodiments are described in sufficient detail to enable those skilled in the art to practice the present subject matter. References to "an", "one", or "various" embodiments in this disclosure are not necessarily to the same embodiment, and such references contemplate more than one embodiment. The following detailed description is demonstrative and not to be taken in a limiting sense. The scope of the present subject matter is defined by the appended claims, along with the full scope of legal equivalents to which such claims are entitled.

Worldwide, coronary artery disease (CAD) is the single most frequent cause of death. Over seven million people die every year from CAD, accounting for 13.2% of all deaths. A major unmet medical need is the peri-procedural diagnosis and treatment of microvascular obstructions (MVO) which occur in 40-60% of STEMI patients treated with a stent. Currently, there is no existing technology which can diagnose and treat MVO while the patient is still in the catheter laboratory after a stent.

The present subject matter provides devices, systems and methods for diagnosing and treating MVO by modeling physiological and pathological conditions. In various embodiments, the present subject matter provides a multi-scale microfluidic model to mimic heart coronary vessels (myocardial microcirculation). Various embodiments incorporate: coronary arterial trees at least or preferentially of the orders 5 throughout 9 (dimensions, orders of coronary vessels), ranging their diameter preferentially from 0.75 mm down to 0.075 mm; coronary collaterals (="natural bypasses") providing alternative pathways bypassing an MVO; coronary artery compliance; showing the spatially resolved fluid transport through the "coronary vessels" (transparent materials); understand the entire blood flow system and validate computer models; simulate a microvascular obstructions (MVO) by rising the flow resistance in one channel or block it completely; and introduce a balloon catheter with pressure sensors and drug delivery device. In various embodiments, behavior of fluid transport in the coronary vessels is modeled and studied during diagnostics or treatment, to design and optimize therapy protocols and thus render animal studies redundant.

Various embodiments of the present subject matter provide a functionally correct bench-top model of coronary circulation, including a model of the myocardial microcirculation. The model reproduces the pulsatile nature of coronary blood flow, provides for systematic study of MVO at different locations and depths in the microcirculation, and features a network of collateral vessels to assess their effect on interventional protocol. The model provides anatomically correct access points for a catheter through the coronary ostia in the aortic root. In addition, the model is transparent to allow for optical access to monitor the progression of infused agents, and it is equipped with pressure and flow sensors at appropriate locations to provide a quantitative understanding of the therapeutic intervention. Previously, experimental evidence was gained by using animal (pig) models with MVO (causing AMI), following a surgery and a magnetic resonance image (MRI). The fluidic model of the present subject matter will make animal studies redundant.

Figure 7A:
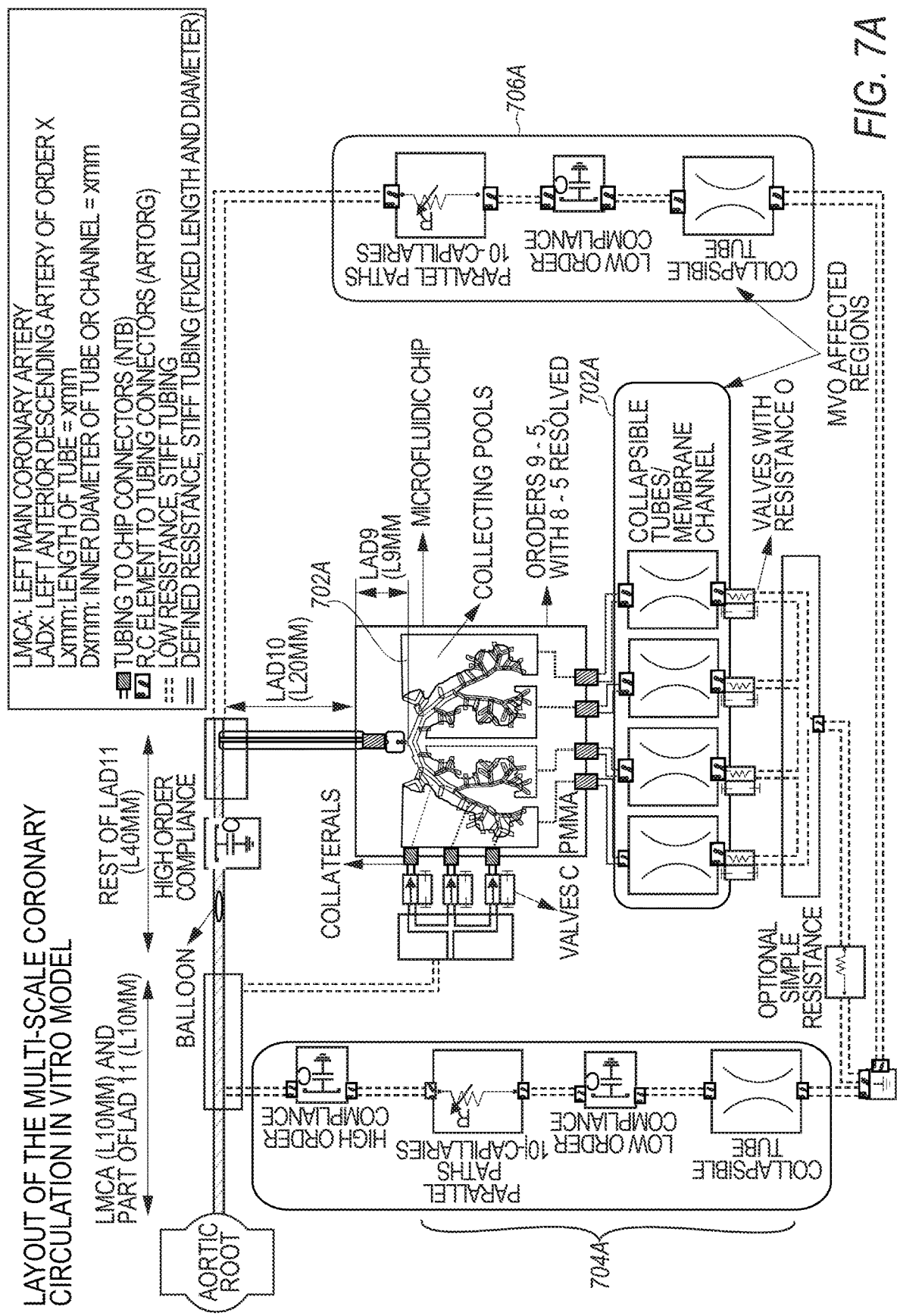
FIG. 7A illustrates a circuit diagram showing a layout of a multi-scale coronary circulation in-vitro model, according to various embodiments.
Figure 7B:
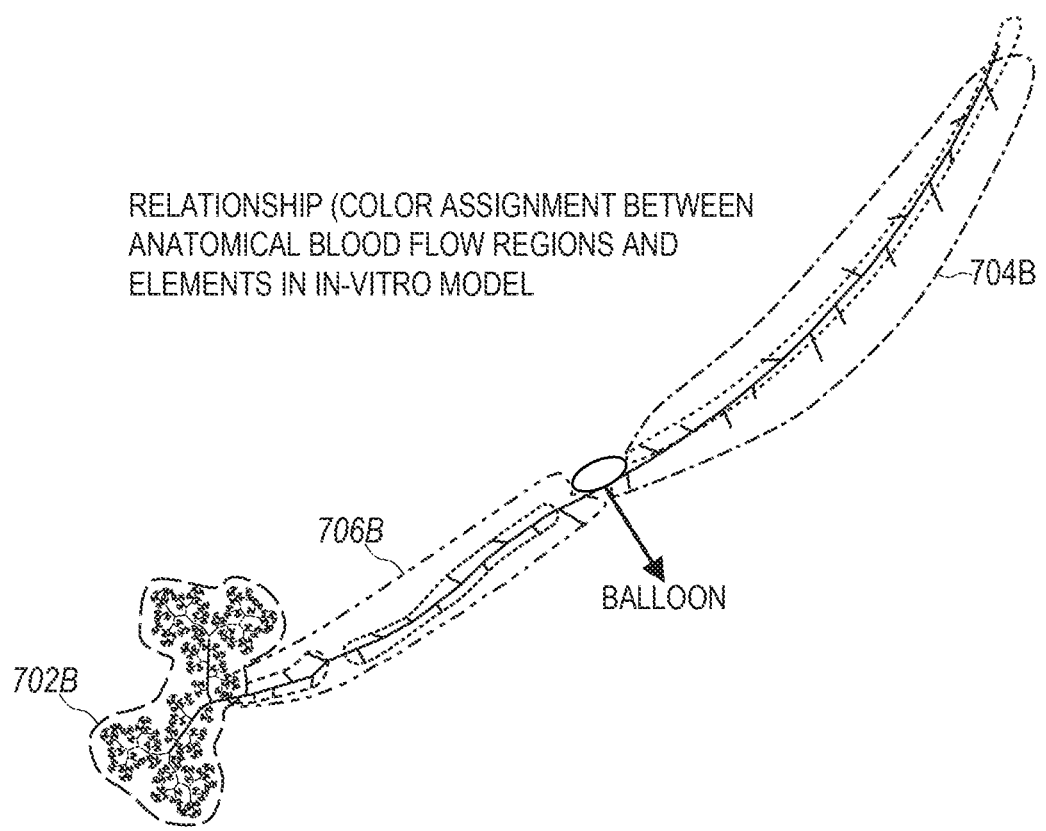
FIG. 7B illustrates anatomical blood flow regions modeled using the model of FIG. 7A, according to various embodiments.
Figure 8A:
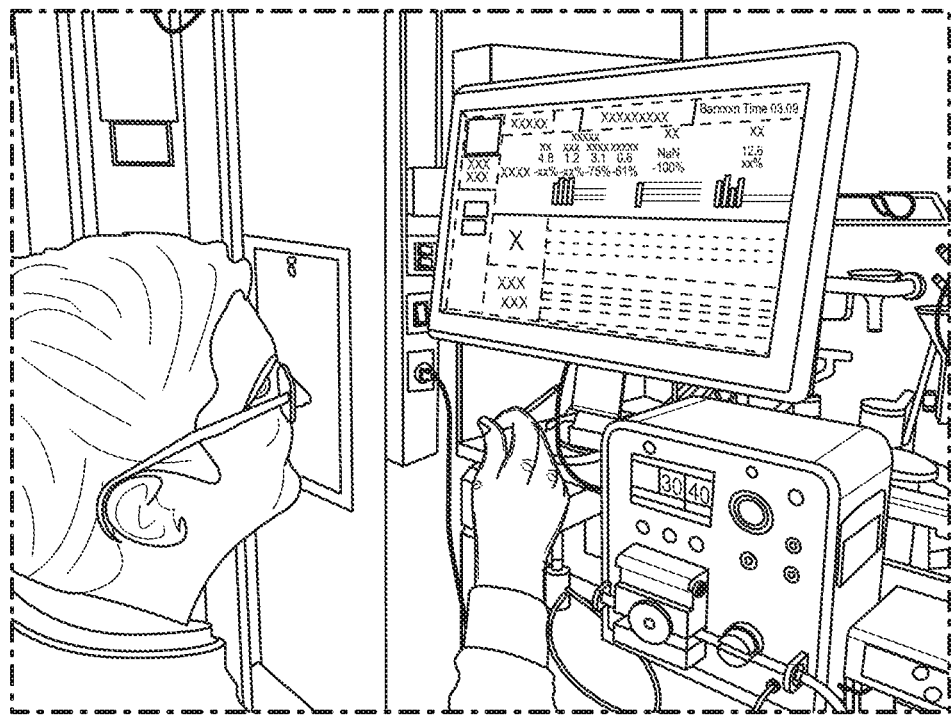
FIG. 8 illustrates graphs showing distal pressure and pump flow for a coronary flow model, according to various embodiments.
Figure 8A:
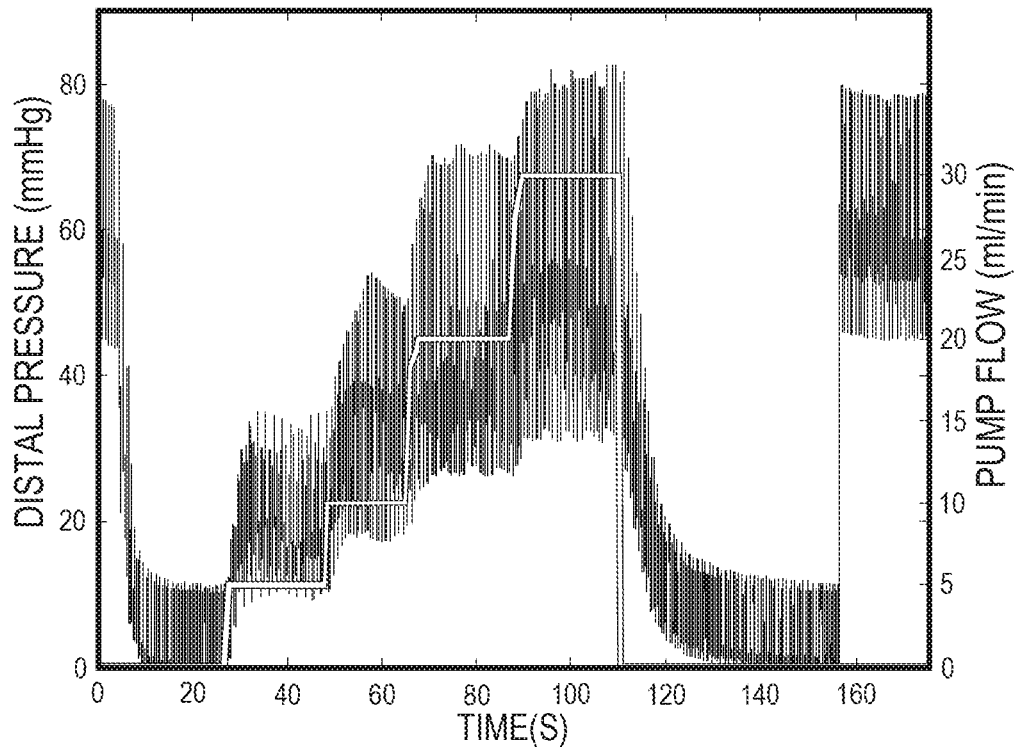
Figure 8B:
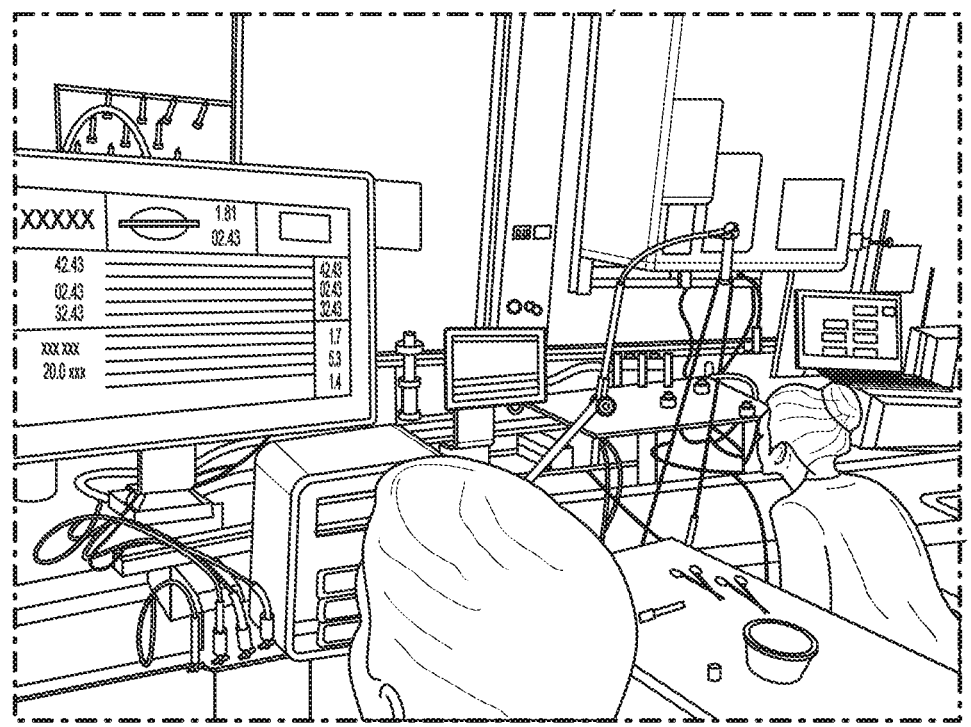
Figure 8B:
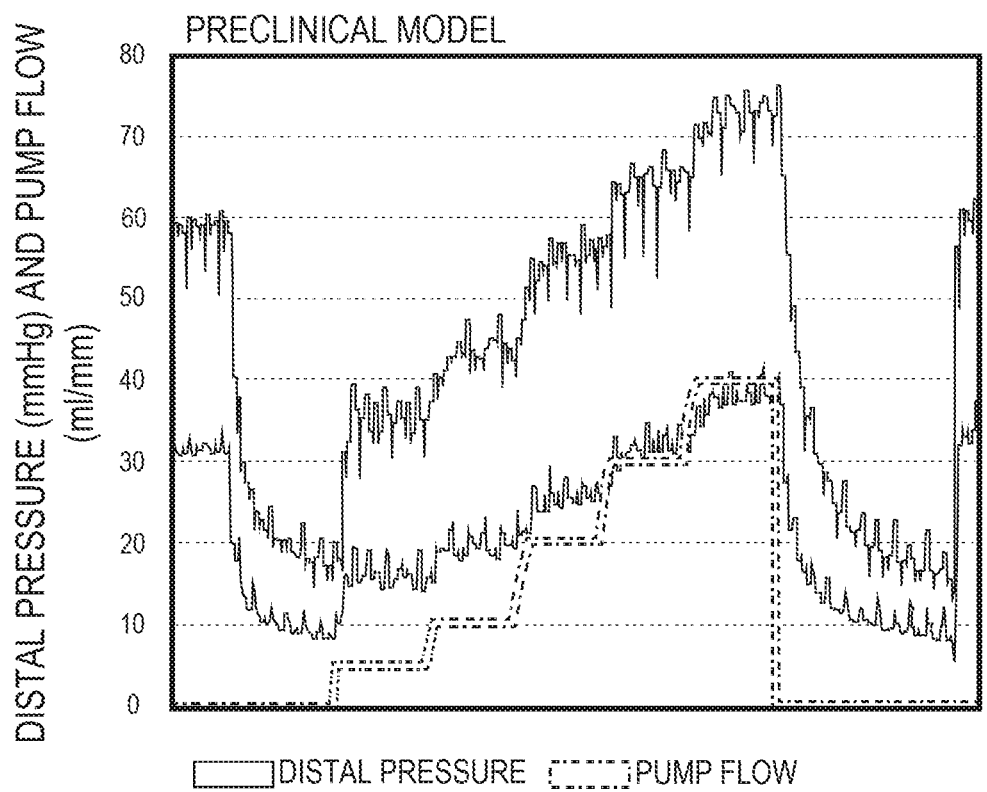

FIG. 1 illustrates an apparatus for MVO diagnosis and therapy, according to various embodiments. The apparatus 100 enables MVO diagnosis by: real-time coronary artery pressure and flow; pressure/resistance time parameters; coronary wedge pressure; intracoronary ECG; with a fractional flow reserve (FFR) included. The apparatus enables MVO therapy by infusion of approved agent(s); targeted and low flow infusion; and continuous monitoring of diagnostic parameters. The microfluidic model is not located on the console, but the catheter is inserted into the coronary model with the balloon positioned as shown in FIGS. 7A and 7B. The coronary model is a patient model, in an embodiment.

Figure 2:
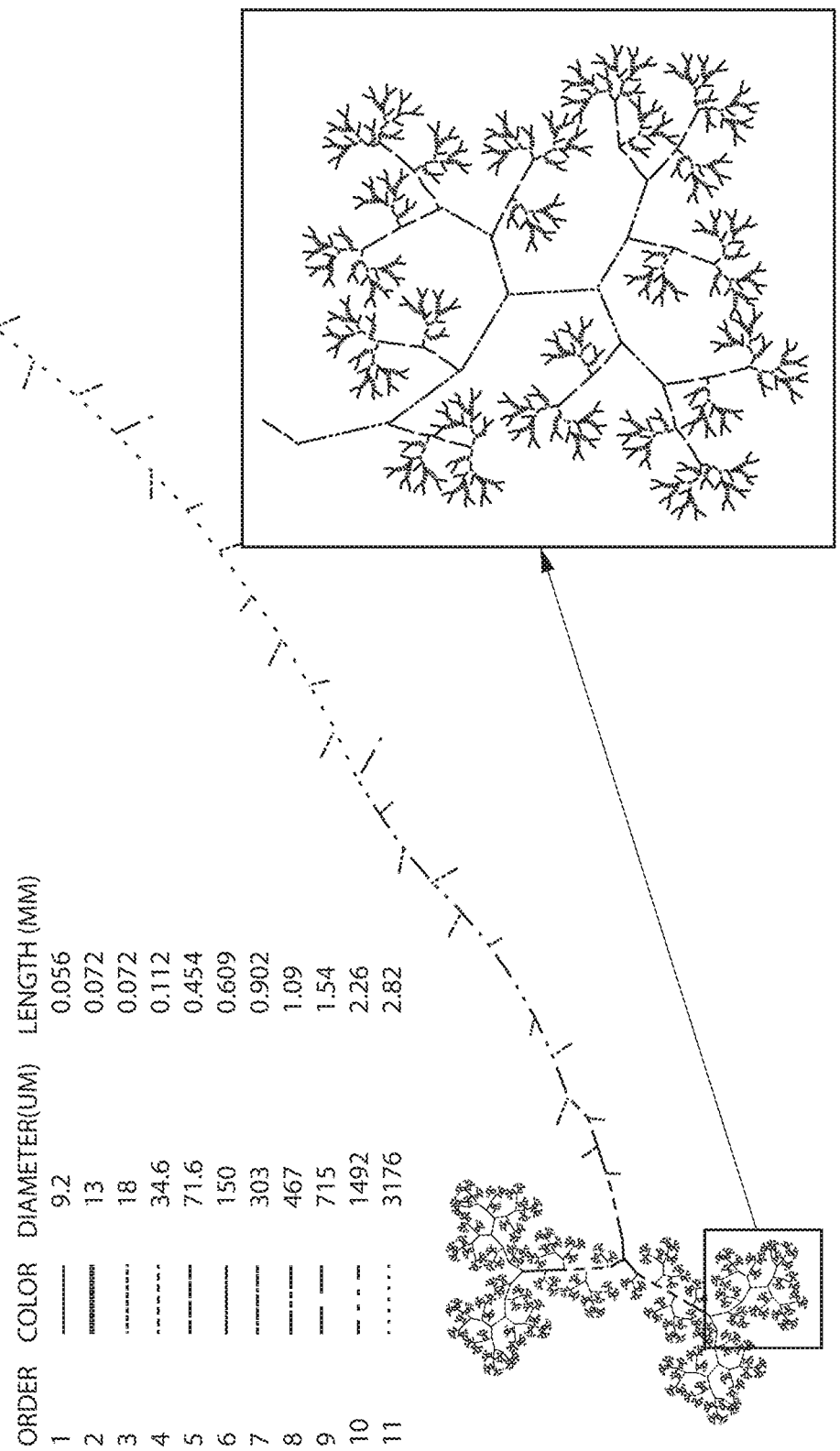
FIG. 2 illustrates connectivity and dimensions of arterial coronary circulation, according to various embodiments.

FIG. 2 illustrates connectivity and dimensions of arterial coronary circulation, according to various embodiments. The depicted embodiment shows an expanded view of a vascular tree of coronary circulation, and includes a table showing geometry of the in-vitro bifurcating coronary model based on a color code used to depict the branches of the vascular tree.

FIG. 3 illustrates morphometry of coronary arterial trees for use in device fabrication, according to various embodiments. The illustration includes a table that shows the order, diameter, length and number of coronary arterial trees, including portions modeled by a microfluidic chip, fittings and tubing, and lumped compliant and valves.

Figure 4:
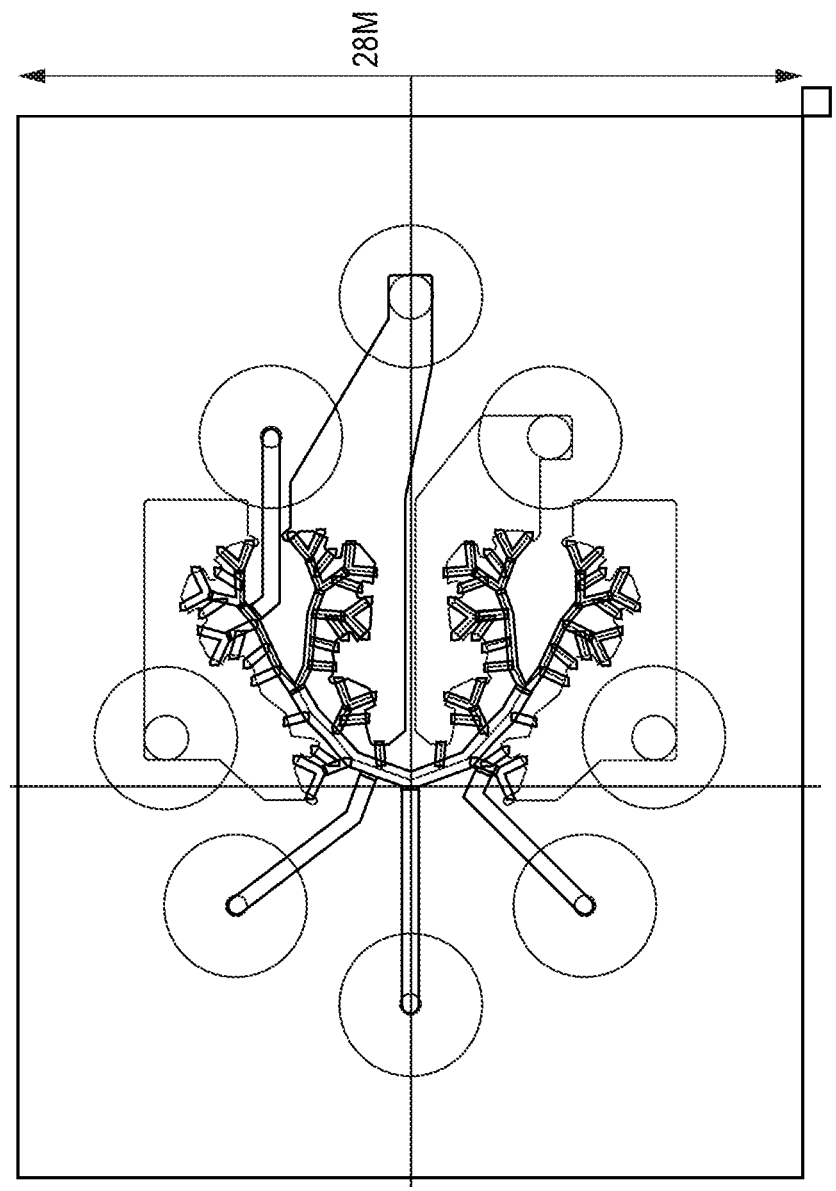
FIG. 4 illustrates a fluidic chip layout used for chip design and fabrication, according to various embodiments.

FIG. 4 illustrates a fluidic chip layout used for chip design and fabrication, according to various embodiments. The illustration includes a layout for a microfluidic model having dimensions of 28 mm by 38 mm, as well as a table showing channel hierarchy and dimensions for an embodiment of a fluid chip layout. The colors used for the channels are indicative of vessel generation/order and each order has a specific mean diameter and length, in the depicted embodiment. In various embodiments, channel cross-sections are semi-circular or circular (as in blood vessels) in the microfluidic chip. In other embodiments, the chip/model has rectangular channels due to manufacturing capabilities, while blood vessels are assumed to be of circular cross-section. The correspondence between the channel height and width and the diameter of actual blood vessels is made via the hydraulic diameter, such that the channels exhibit a similar hydraulic resistance per length as blood vessels of a specific order. The length of each channel order is the same as the mean length of coronaries of that order, in various embodiments. Thus, colors in FIGS. 2, 3 and 4 are indicative of the diameter and length of coronary blood vessels of different orders and of the hydraulic diameter and length of the corresponding channels. The table in FIG. 4 relates the hydraulic diameter to the actual channel dimensions.

Figure 5:
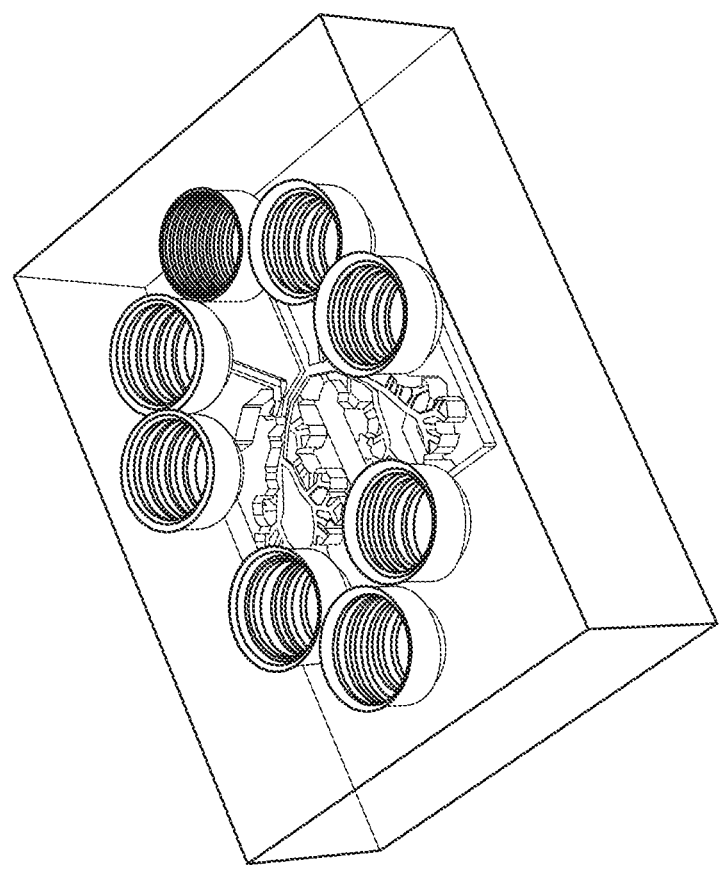
FIG. 5 illustrates a photograph of a fluidic chip after micromilling and thermocompressive bonding, according to various embodiments.
Figure 5:
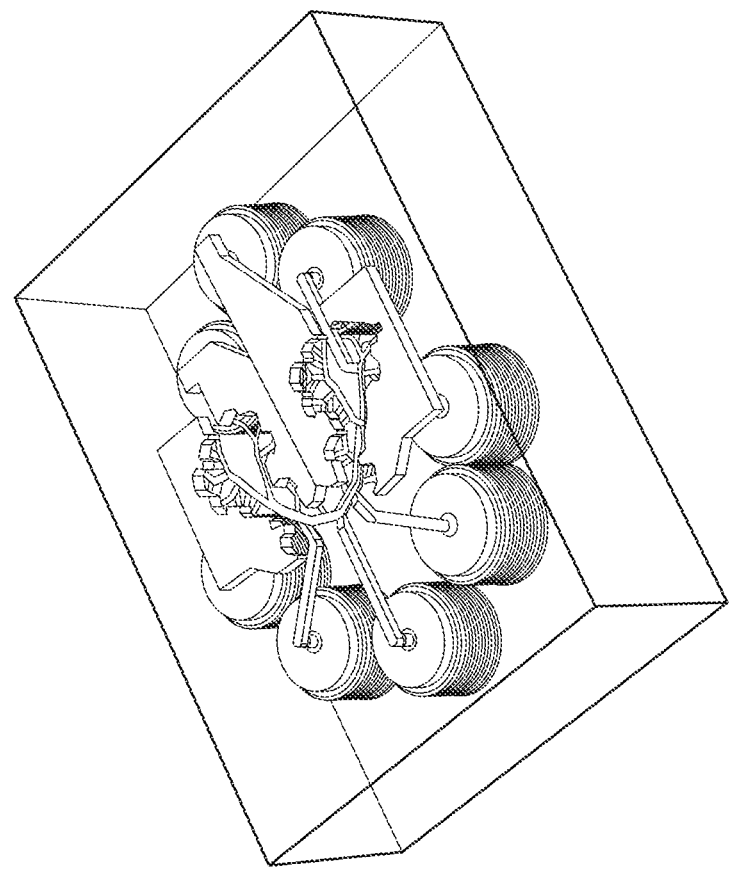
Figure 6:
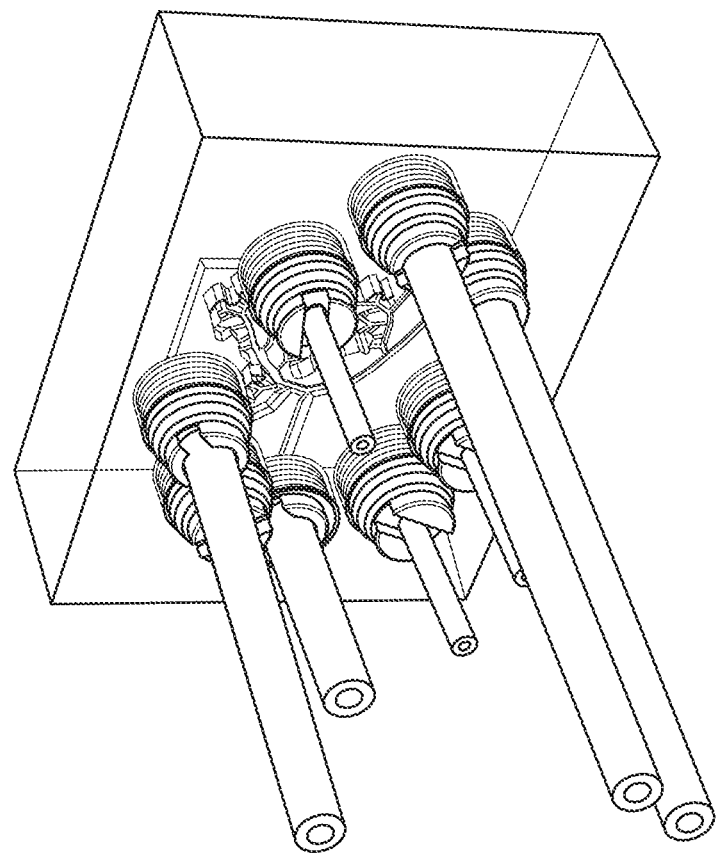
FIG. 6 illustrates a photograph of a fluidic chip after assembly of tubing with fittings, according to various embodiments.
Figure 6:
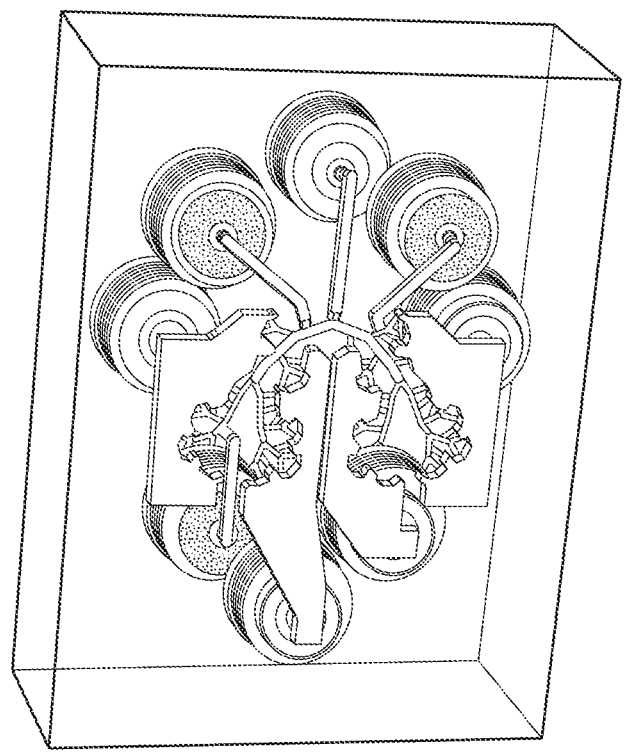

FIG. 5 illustrates a photograph of a fluidic chip after micromilling and thermocompressive bonding, according to various embodiments. Ports and fitting locations of the respective portions of the microfluidic model are shown in the illustration. FIG. 6 illustrates a photograph of a fluidic chip after assembly of tubing with fittings, according to various embodiments. In various embodiments, the fluidic chip includes a layer construction. In some embodiments, the fluidic chip includes thick and rigid layers called substrates. Optionally, thin foils or laminates can be used as an interlayer or interlayers. The chip stacking is not limited to a thermal bonding hierarchy, allowing for multiple stacking of substrates and interlayers, in various embodiments. Some embodiments use a transparent thermoplastic such as polymethyl methacrylate (PMMA). Various embodiments include PMMA-PMMA stacks, and further embodiments use PMMA-Elastosil-PMMA stacks or substrates. In various embodiments, the substrates can be made of polymers, metals, glasses, or ceramics. In still further embodiments, the substrates can be made of titanium. In other embodiments, an interlayer of silicone with its high elasticity can be used. Materials such as polydimethyisiloxane (PDMS) can be used in some embodiments. In some embodiments, membranes with even higher elasticity, such as biomembranes, can be used in a stack for the fluidic chip. Other materials or combinations of materials can be used without departing from the scope of the present subject matter. In various embodiments, a membrane of the stack can be either patterned or unpatterned. The patterning of the membrane can be subtractive by etching or additive by three-dimensional printing, in various embodiments. In the latter case elastic acrylic-compounds can be used for the membrane. In an embodiment, a microfluidic chip is fabricated out of PMMA and silicone, but other materials can be used, such as glass and PDMS or other polymers that are employed in microfluidic applications.

FIG. 7A illustrates a circuit diagram showing a layout of a multi-scale coronary circulation model, according to various embodiments. The depicted embodiment highlights MVO affected regions modeled using variable resistance and collapsible tubes. Connections to the aortic root include left main coronary artery (LMCA) portions and left anterior descending artery of order x (LADx) are depicted, including a 20 mm tube to model LAD10 in this embodiment. The microfluidic chip includes collecting pools and collaterals used for connections to valves and collapsible tubes. FIG. 7B illustrates anatomical blood flow regions modeled using the model of FIG. 7A, according to various embodiments. A relationship between anatomical blood flow regions 702B, 704B, 706B in FIG. 7B and elements in the in-vitro model 702A, 704A, 706A in FIG. 7A is shown using color and shading in the diagrams. Also depicted are tubing to chip connectors, resistance element to tubing connectors, low resistance stiff tubing, and defined resistance stiff tubing of fixed length and diameter.

FIG. 8 illustrates graphs showing distal pressure and pump flow for a coronary flow model, according to various embodiments. A preclinical (pig testing) model graph is shown, in comparison with a bench-top model graph that is based on experiments conducted using the coronary flow model, in various embodiments. In some embodiments, the bench-top model of the present subject matter and the preclinical model are complementary strategies, especially for a pathology with complex hemodynamic consequences that are not known a priori. In the preclinical model blood flow and drug delivery in microvessels can only be derived from large scale phenomena, such as resistance measurements in large coronaries (catheter), or from clinical imaging modalities (such as cardiovascular magnetic resonance imaging (CMR) or angiographic imaging) of limited spatial and temporal resolution. In the bench-top model of the present subject matter, the parameters of interest can be studied and measured down to the level of a single microvessel either by flow visualization or sensor integration. Thus, the bench-top model is used to relate large scale observations made in the preclinical model to the phenomena occurring in individual microvessels. This is not only important to investigate disease mechanisms, but also to understand the working principle of the medical device, while also providing a platform to test different interventional protocols in a safe and cost-effective manner. Also, the bench-top model can be easily adapted to reflect different manifestations of the disease, vascular anatomies and cardiac properties, whereas such parameters are difficult or even impossible to control in the preclinical model. Therefore, the bench-top model is also used to test the performance of the medical device in different patient models, in various embodiments.

Figure 9:
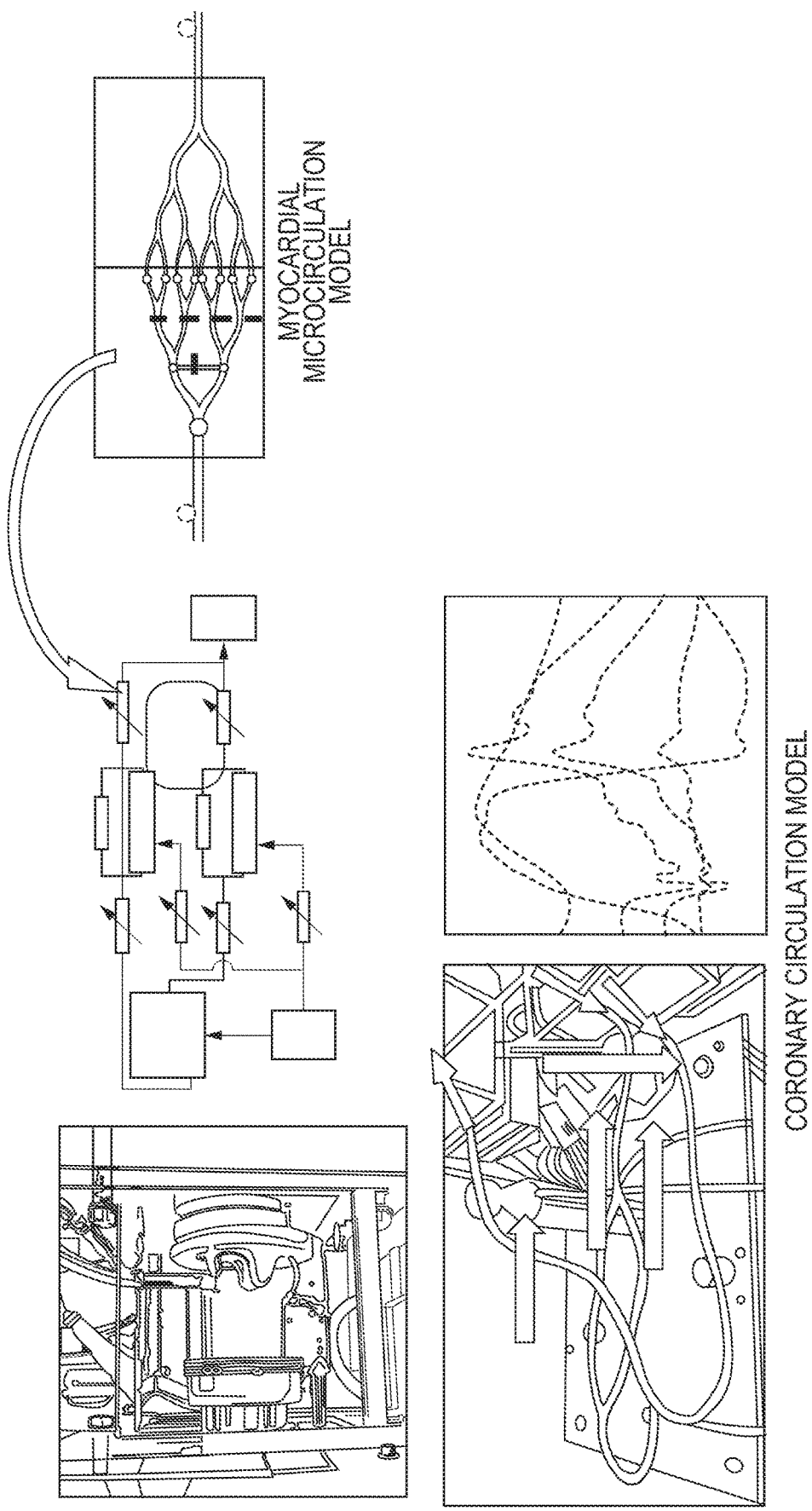
FIG. 9 illustrates a myocardial microcirculation model, according to various embodiments.

FIG. 9 illustrates a myocardial microcirculation model according to various embodiments. The depicted embodiment is used to model physiological and pathological conditions for a portion of a coronary circulation model. On the arterial side, valves are used to adjust flow resistance, and sensors are used to measure flow and pressure in vessels, including a collateral branch.

Figure 10:
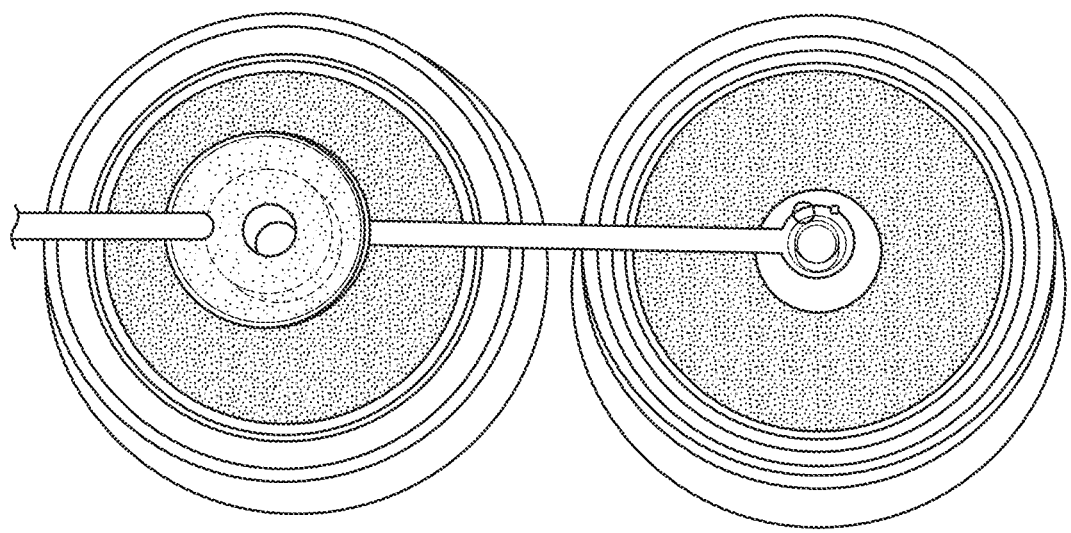
FIG. 10 illustrates ports used in flow measurements for a valve of a microfluidic model, according to various embodiments.
Figure 10:
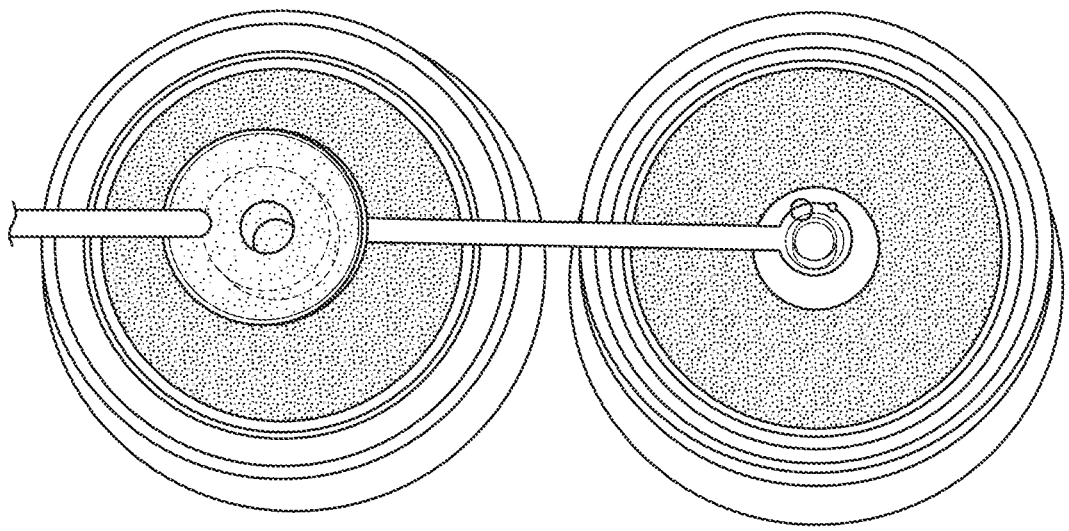

FIG. 10 illustrates ports used in flow measurements for a valve of a microfluidic model, according to various embodiments. The ports are tight such that bubbles are not incorporated in the fluidic paths, in various embodiments. In the depicted embodiment, the pair of ports on the right side are similar to the pair on the left, the only difference is the deflection of the membrane inside the chip. The left port in each pair is the inlet and the right one is the outlet, in the depicted embodiment. An actuated valve and a pneumatically actuated membrane are components used in measurements for a valve of a microfluidic model, including membrane diameter, membrane thickness, pressure at the port, and displacement at the center of the membrane, in various embodiments.

The flow through the valve can be controlled down to a minimal flow of less than 1%, as shown by the above measurements. In addition, flow control can be accomplished in a wide linear range. The closing pressure of the valves measured are within tight tolerances at 22 mbar+/−1 mbar, in various embodiments. The flow characteristic in the positive direction is free of hysteresis. Vibration of the membrane in the reverse direction is identified in the above measurements. The pressure-dependent compliance is measured, and the measured values are in agreement with the calculations and targeted specifications. The valves can be pressurized up to 700 mbar without showing an increase of the leakage rate.

Figure 11A:
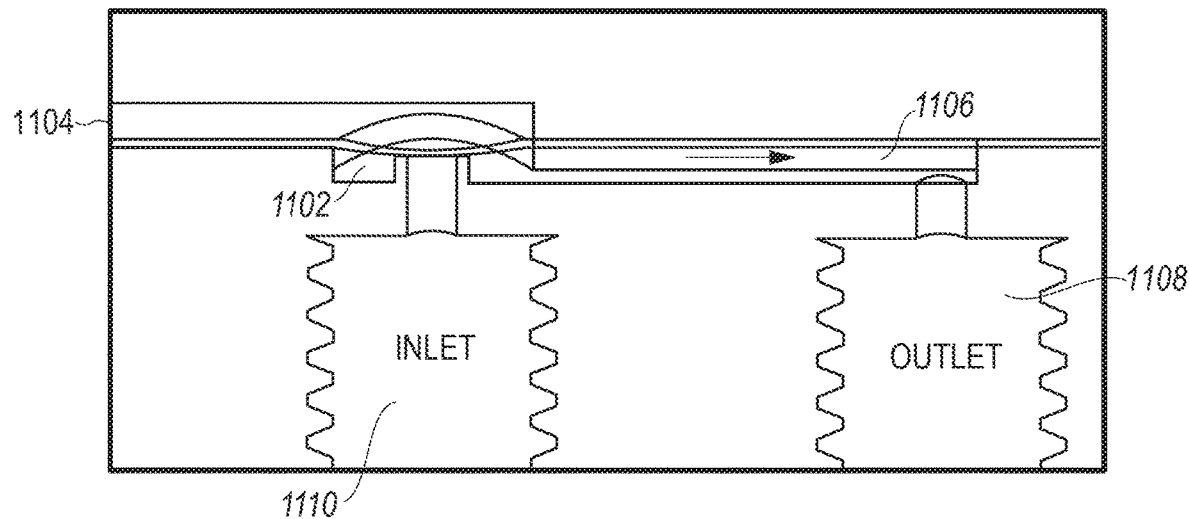
FIGS. 11A-11C illustrate a microfluidic model including a membrane which is pressurized from left ventricle pressure to occlude the microcirculatory vessels in systole, according to various embodiments.
Figure 11B:
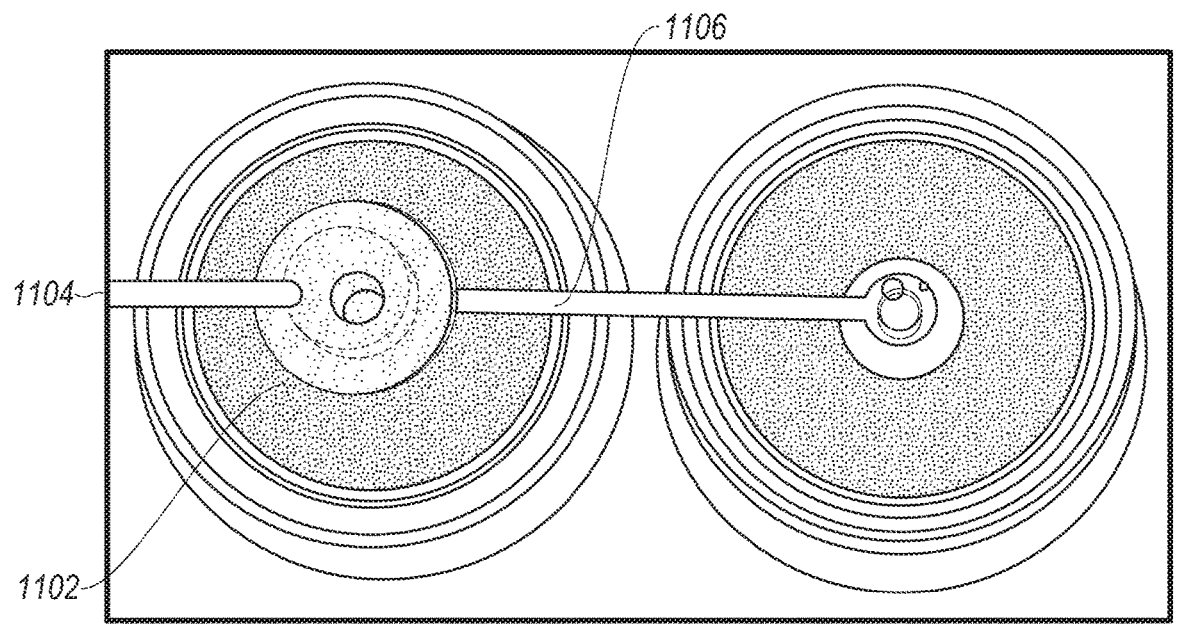
Figure 11C:
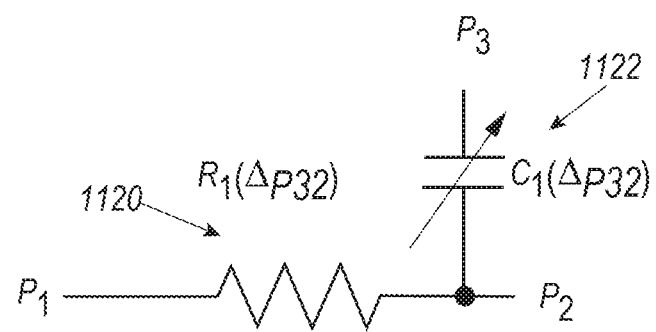

FIGS. 11A-11C illustrate a microfluidic model including a membrane which is pressurized from left ventricle pressure to occlude the microcirculatory vessels in systole, according to various embodiments. In FIG. 11A, the membrane 1102 may be activated to model elasticity of a vessel wall. In one embodiment, the membrane 1102 is a silicone membrane. Other materials can be used without departing from the scope of the present subject matter. In various embodiments, the membrane 1102 is an interface between a control channel 1104 and a fluid channel 1106 between an inlet 1110 and an outlet 1108. The membrane 1102 provides a simulation of narrowing of a vessel, and the membrane 1102 includes a variable elasticity that can be adjusted to mimic diseases such as atherosclerosis, in various embodiments. FIG. 11B illustrates an example electrical circuit used to represent the model of FIG. 11A, including a variable capacitance 1122 and a variable resistance 1120. FIG. 11C is a top view of the membrane included in the microfluidic model of the present subject matter. In various embodiments, an elastic vessel wall is represented by pneumatically actuated silicone membrane. Variable channel cross section represents the narrowing of vessels, in various embodiments.

Example 1 is a system for modeling a microvascular obstruction (MVO), the system comprising: a multi-scale model configured to mimic myocardial microcirculation of coronary vessels, the multi-scale model including collaterals configured to model coronary arterial trees, wherein the collaterals are configured to provide alternative pathways bypassing the MVO, and configured to model coronary artery compliance for spatially resolved fluid transport through the coronary vessels: wherein the multi-scale model is configured to simulate the MVO by increasing flow resistance in at least one of the modeled coronary vessels.

In Example 2, the subject matter of Example 1 is optionally configured such that the multi-scale model is configured to simulate the MVO by blocking the at least one of the modeled coronary vessels completely.

In Example 3, the subject matter of Example 1 or 2 is optionally configured such that the multi-scale model is configured to mimic behavior of fluid transport in the coronary vessels during diagnostics.

In Example 4, the subject matter of Example 1 or 2 is optionally configured such that the multi-scale model is configured to mimic behavior of fluid transport in the coronary vessels during treatment.

In Example 5, the subject matter of Example 4 is optionally configured such that the multi-scale model is configured to be used to design therapy protocols for the MVO.

In Example 6, the subject matter of Example 4 is optionally configured such that the multi-scale model is configured to be used to optimize therapy protocols for the MVO.

In Example 7, the subject matter of any of Examples 1-6 is optionally configured such that the collaterals are configured to model coronary arterial trees of at least or preferentially the orders 5 throughout 9 of coronary vessels.

In Example 8, the subject matter of Example 7 is optionally configured such that the collaterals are configured to model coronary arterial trees ranging in diameter from 0.75 mm to 0.075 mm.

In Example 9, the subject matter of any of Examples 1-8 is optionally configured such that the multi-scale model includes multiple layers.

In Example 10, the subject matter of Example 9 is optionally configured such that the multiple layers include one or more of polymers, metals, glasses or ceramics.

In Example 11, the subject matter of Example 9 is optionally configured such that the collaterals are formed by etching one or more of the multiple layers.

Example 12 is a method for modeling a microvascular obstruction (MVO), the method comprising: modeling myocardial microcirculation of coronary vessels using a multi-scale model, the multi-scale model including collaterals configured to model coronary arterial trees, wherein the collaterals are configured to provide alternative pathways bypassing the MVO, and configured to model coronary artery compliance for spatially resolved fluid transport through the coronary vessels; and simulating the MVO by increasing flow resistance in at least one of the modeled coronary vessels.

In Example 13, the subject matter of Example 12 is optionally configured such that the method comprises using the multi-scale model to simulate the MVO by blocking the at least one of the modeled coronary vessels completely.

In Example 14, the subject matter of Example 12 or 13 is optionally configured such that the method comprises using the multi-scale model to mimic behavior of fluid transport in the coronary vessels during diagnostics.

In Example 15, the subject matter of Example 12 or 13 is optionally configured such that the method comprises using the multi-scale model to mimic behavior of fluid transport in the coronary vessels during treatment.

Example 16 is an apparatus for modeling a microvascular obstruction (MVO), the apparatus comprising: a fluidic chip configured to mimic myocardial microcirculation of coronary vessels; and collaterals within the fluidic chip, the collaterals configured to model coronary arterial trees, wherein the collaterals are configured to provide alternative pathways bypassing the MVO, the collaterals configured to model coronary artery compliance for spatially resolved fluid transport through the coronary vessels; wherein the apparatus is configured to simulate the MVO by increasing flow resistance in at least one of the modeled coronary vessels.

In Example 17, the subject matter of Example 16 is optionally configured such that the fluidic chip includes one or more layers of substrates.

In Example 18, the subject matter of Example 17 is optionally configured such that the collaterals are formed by etching the one or more layers of substrates.

In Example 19, the subject matter of any of Examples 16-18 is optionally configured such that the fluidic chip includes one or more layers of thin foils configured to be used as interlayers.

In Example 20, the subject matter of any of Examples 16-18 is optionally configured such that the fluidic chip includes one or more layers of laminates configured to be used as interlayers.

Example 21 is a system for modeling a microvascular obstruction (MVO), the system comprising a multi-scale model configured to mimic myocardial microcirculation of coronary vessels, the multi-scale model including collaterals configured to model coronary arterial trees, wherein the collaterals are configured to provide alternative pathways bypassing the MVO, and configured to model coronary artery compliance for spatially resolved fluid transport through the coronary vessels; wherein the multi-scale model is configured to simulate the MVO by increasing flow resistance in at least one of the modeled coronary vessels, and wherein the multi-scale model includes a membrane which is pressurized from left ventricle pressure to occlude the vessels in systole.

Example 22 is at least one machine-readable medium including instructions that, when executed by processing circuitry, cause the processing circuitry to perform operations to implement of any of Examples 1-21.

Example 23 is an apparatus comprising means to implement of any of Examples 1-21.

Example 24 is a system to implement of any of Examples 1-21.

Example 25 is a method to implement of any of Examples 1-21.

The foregoing examples are not limiting or exclusive, and the scope of the present subject matter is to be determined by the specification as a whole, including the claims and drawings.

The above description includes references to the accompanying drawings, which form a part of the detailed description. The drawings show, by way of illustration, varying embodiments in which the invention can be practiced. The application also refers to "examples." Such examples can include elements in addition to those shown or described. The foregoing examples are not intended to be an exhaustive or exclusive list of examples and variations of the present subject matter.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description.

The scope of the invention should be determined with reference to the appended claims, along with the full scope of equivalents to which such claims are entitled.

What is claimed is:

1. A bench-top system for modeling a microvascular obstruction (MVO), the bench-top system comprising:
a physical multi-scale model configured to mimic myocardial microcirculation of coronary vessels, the physical multi-scale model including collaterals configured to model coronary arterial trees, wherein the collaterals are configured to provide alternative pathways bypassing the MVO, and configured to model coronary artery compliance for spatially resolved fluid transport through the coronary vessels;
wherein at least one of the modeled coronary vessels comprises a collapsible tube or a membrane, the at least one of the modeled coronary vessels having variable resistance, and
wherein the physical multi-scale model is configured to simulate the MVO by increasing flow resistance in the at least one of the modeled coronary vessels.

2. The bench-top system of claim 1, wherein the physical multi-scale model is configured to simulate the MVO by blocking the at least one of the modeled coronary vessels completely.

3. The bench-top system of claim 1, wherein the physical multi-scale model is configured to mimic behavior of fluid transport in the coronary vessels during diagnostics.

4. The bench-top system of claim 1, wherein the physical multi-scale model is configured to mimic behavior of fluid transport in the coronary vessels during treatment.

5. The bench-top system of claim 4, wherein the physical multi-scale model is configured to be used to design therapy protocols for the MVO.

6. The bench-top system of claim 4, wherein the physical multi-scale model is configured to be used to optimize therapy protocols for the MVO.

7. The bench-top system of claim 1, wherein the collaterals are configured to model coronary arterial trees of at least the orders 5 throughout 9 of coronary vessels.

8. The bench-top system of claim 7, wherein the collaterals are configured to model coronary arterial trees ranging in diameter from 0.75 mm to 0.075 mm.

9. The bench-top system of claim 1, wherein the physical multi-scale model includes multiple layers.

10. The bench-top system of claim 9, wherein the multiple layers include one or more of polymers, metals, glasses or ceramics.

11. The bench-top system of claim 9, wherein the collaterals are formed by etching one or more of the multiple layers.

12. A method for modeling a microvascular obstruction (MVO), the method comprising:
modeling myocardial microcirculation of coronary vessels using a multi-scale model, the multi-scale model including collaterals configured to model coronary arterial trees, wherein the collaterals are configured to provide alternative pathways bypassing the MVO, and configured to model coronary artery compliance for spatially resolved fluid transport through the coronary vessels, wherein at least one of the modeled coronary vessels comprises a collapsible tube or a membrane, the at least one of the modeled coronary vessels having variable resistance; and
simulating the MVO by increasing flow resistance in the at least one of the modeled coronary vessels.

13. The method of claim 12, comprising using the multi-scale model to simulate the MVO by blocking the at least one of the modeled coronary vessels completely.

14. The method of claim 12, comprising using the multi-scale model to mimic behavior of fluid transport in the coronary vessels during diagnostics.

15. The method of claim 12, comprising using the multi-scale model to mimic behavior of fluid transport in the coronary vessels during treatment.

16. An apparatus for modeling a micro vascular obstruction (MVO), the apparatus comprising:

a fluidic chip configured to mimic myocardial microcirculation of coronary vessels; and collaterals within the fluidic chip, the collaterals configured to model coronary arterial trees, wherein the collaterals are configured to provide alternative pathways bypassing the MVO, the collaterals configured to model coronary artery compliance for spatially resolved fluid transport through the coronary vessels;

wherein at least one of the modeled coronary vessels comprises a collapsible tube or a membrane, the at least one of the modeled coronary vessels having variable resistance, and wherein the apparatus is configured to simulate the MVO by increasing flow resistance in the at least one of the modeled coronary vessels.

17. The apparatus of claim 16, wherein the fluidic chip includes one or more layers of substrates.

18. The apparatus of claim 17, wherein the collaterals are formed by etching the one or more layers of substrates.

19. The apparatus of claim 16, wherein the fluidic chip includes one or more layers of thin foils configured to be used as interlayers.

20. The apparatus of claim 16, wherein the fluidic chip includes one or more layers of laminates configured to be used as interlayers.

21. A bench-top system for modeling a microvascular obstruction (MVO), the bench-top system comprising:

a physical multi-scale model configured to mimic myocardial microcirculation of coronary vessels, the physical multi-scale model including collaterals configured to model coronary arterial trees, wherein the collaterals are configured to provide alternative pathways bypassing the MVO, and configured to model coronary artery compliance for spatially resolved fluid transport through the coronary vessels;

wherein the physical multi-scale model is configured to simulate the MVO by increasing flow resistance in at least one of the modeled coronary vessels, and wherein the physical multi-scale model includes a membrane which is pressurized from left ventricle pressure to occlude the vessels in systole.

* * * * *